United States Patent [19]
Wollschläger et al.

[11] Patent Number: 5,105,819
[45] Date of Patent: Apr. 21, 1992

[54] ULTRASOUND ENDOSCOPE DEVICE

[75] Inventors: Helmut Wollschläger; Susanna Wollschläger; Andreas Zeiher, all of Freiburg; Hans-Peter Klein, Ebersberg, all of Fed. Rep. of Germany

[73] Assignee: Kon-Tron Elektronik AG, Eching, Fed. Rep. of Germany

[21] Appl. No.: 663,903

[22] PCT Filed: Aug. 23, 1989

[86] PCT No.: PCT/DE89/00551
§ 371 Date: Apr. 16, 1991
§ 102(e) Date: Apr. 16, 1991

[87] PCT Pub. No.: WO90/02520
PCT Pub. Date: Mar. 22, 1990

[30] Foreign Application Priority Data

Sep. 1, 1988 [DE] Fed. Rep. of Germany ....... 3829603

[51] Int. Cl.⁵ .............................. A61B 8/12; A61B 1/00
[52] U.S. Cl. ...................... 128/662.06; 128/4

[58] Field of Search ............... 128/662.06, 4, 660.03; 73/623; 604/96–103

[56] References Cited

U.S. PATENT DOCUMENTS

| | | | |
|---|---|---|---|
| 4,543,960 | 10/1985 | Harui et al. | 128/662.06 |
| 4,561,446 | 12/1985 | Hetz | 128/662.06 |
| 4,756,313 | 7/1988 | Terwilliger | 128/662.06 |
| 4,819,650 | 4/1989 | Goldstein | 128/662.06 X |
| 5,002,059 | 3/1991 | Crowley et al. | 128/662.06 |

Primary Examiner—Francis Jaworski
Attorney, Agent, or Firm—Michael J. Hughes

[57] ABSTRACT

An ultrasonic endoscope device for scanning a patient's organ is constructed using a mobile ultrasonic transducer probe on a carriage housed in a distal and section of the device, within a guide channel formed by a plurality of axially aligned rigid guide links having hollow spaces opened to one side and pivotable by means of a tension wire running through the links. A flexible hose in conjunction with a balloon envelope surround the end section and serves as a water supply path. The device is especially useful for transeophaged echocardiographic scanning.

9 Claims, 8 Drawing Sheets

ULTRASOUND ENDOSCOPE DEVICE

TECHNICAL FIELD

This invention is in regard to an ultrasound endoscope device for scanning the patient's organ in question, in particular, for use in transesophageal echo cardiography with an ultrasound converter which is electrically connected via an ultrasound diagnostic device to an image processing system for producing multiplanar tomograms, and which is arranged in a mobile manner in the endoscope's distal end section.

BACKGROUND ART

Such an arrangement is known from the publication by Roy W. Martin et al., "An Endoscopic Micromanipulator for Multiplanar Transesophageal Imaging, Ultrasound in Med. & Biol., Vol. 12, No. 12, pp. 965-975, 1986", and is used for three-dimensional reconstructive ultrasound imaging of the heart by taking multiplanar, sectional images with the help of an ultrasound converter which is located at the endoscope's front end and capable of a slewing motion perpendicular to the endoscope's longitudinal axis. The planes of the sectional images obtained in this manner are at oblique angles to each other. The result is that the imaging data gained lacks the necessary quality for some applications and the scanned volume is small and its distribution unfavorable. Above all, the scans are not precise enough for reproduction and the images generated are unsuitable for comparative studies.

From U.S. Pat. No. 4,327,738, an endoscopic process as well as a device for Ultrasound-B-Image scans are known. The ultrasound converter is arranged in the rigid front end of an otherwise flexible hose. In order to generate multiplanar tomograms, position changes are required which are difficult to reproduce, and as a consequence, exact three-dimensional reconstructions of the scanned organs are not possible.

From EP-A1-0 234 951, a catheter with an ultrasound converter is known which allows the scanning of blood vessels by slewing the ultrasound converter on its longitudinal axis and/or by its lengthwise extension. However, the reproducibility of the tomograms obtained in this manner is equally poor and, consequently, exact three-dimensional reconstructions of the scanned organs are not possible.

From U.S. Pat. No. 4,686,963, an inspection instrument with a long flexible body is known which has a number of hollow links arranged in axial alignment, forming a guiding channel for fibre-optic strands. In order to give the device rigidity, a tension wire runs through the links and presses them together.

In GB-A-2 143 920, an endoscope shaft is described which also consists of a number of vertebrae-like links surrounded by a flexible hose.

DISCLOSURE OF INVENTION

Departing from the state of the art, the invention is based on the task of creating an ultrasound endoscope device as described above which will allow very precise multplanar scans of a large volume of the organ's area in question and to obtain image sections which will permit an exact reconstruction of the scanned organ.

The problem of creating such an an endoscope device is solved by the fact that a flexible hose with a balloon envelope serving as a water supply line surrounds the endoscope's distal end section and contains a number of axially aligned rigid guide links which have hollow spaces open to one side in the direction of the sound projection and side walls which form a continuous guide channel for a mobile carriage carrying the ultrasound converter led by guide elements through the one-sidedly open hollow spaces, and that a tension wire runs through the guide links by which the guide links can be pressed together at their faces, and that the proximal end of the endoscope's tube is connected to a manipulator device by which a Bowden cable assigned to the tension wire, and a Bowden cable assigned to the carriage, can be activated, and that the manipulator device has a water supply fitting through which water can be supplied to the distal end section via a tube.

By making the distal end of the ultrasound endoscope a flexible hose surrounding and containing a number of rigid guide links, it is possible to insert the endoscope device into the patient's curved body cavities, especially into the esophagus. When the individual guide links are pulled together by means of the tension wire, they provide a rigid guide rail for the ultrasound converter's carriage which can then be moved with great precision over some distance to obtain a large number of parallel, stratified planar images. With the help of the imaging system connected to the ultrasound converter, the individual images can be assembled into a three-dimensional total picture with a precision that will allow comparative study of the single sections. Because of the parallel alignment of the individual sound planes perpendicularly to the longitudinal axis of the ultrasound endoscope device, it is possible, in addition, to recognize the heart's movements and possible disorders caused by pathological conditions. In this procedure, the sectional scanning can be triggered by an EKG, and the carriage advanced after each heart action by a 256th part of the total scanning path, so that oy using a matrix size of 256×256 picture points, a picture cube will be the result. This data can be stored in the imaging system's memory and subsequently viewed, measured, and quantified from any desired view point without any loss of resolution. In addition, EKG-triggered images of an entire heart action on each sectional plane are possible, resulting at the end of the scanning path in a number of picture cubes that corresponds to the number of scans in each sectional plane and allows the dynamics of a freely selective evaluation from any perspective.

For a reproducible evaluation of the sectional planes and for a three-dimensional reconstruction of the heart structures based on the information gained, it is important to know the exact position of the ultrasound endoscope device and the planes of the sound signals inside the body. By providing the carriage with an inductance coupling and by placing at the outside of the patient's body two level coils at a right angle to each other to produce defined magnetic fields, it is possible to determine the exact planar scanning positions based on an external coordinate system. The echo data information from the parallel, two-dimensional sectional planes can then be converted into absolute values in a fixed three-dimensional coordinate system based on the relative position of the ultrasound endoscope device.

Following this procedure, it is possible for the first time to obtain reproducible topographic information about the heart and its movements by echo-cardiography. By monitoring the sound detecting device externally, and by converting the echo data obtained into absolute three-dimensional coordinates, the resulting information is independent of the heart's position inside the ribcage and can be used to make reliable assessments of a progressive heart condition on one hand, and to refer to the data obtained for comparative study on the other. Movements of the esophagus relative to to heart are no longer of any consequence when the respective position of the ultrasound endoscope device is known for each of the scans and its location can be taken into account when evaluating the picture. In summary, thanks to the ultrasound endoscope device according to this invention, it is possible to obtain a three-dimensional reconstruction of the ultrasound image of a heart that is independent of the heart's position inside the ribcage and independent of the esophagus' position relative to the heart. Until now, such examinations were possible only by more costly procedures, such as, for example, angiography, computer, and nuclear spin tomography, whereby these procedures have, besides their significantly higher cost, the additional disadvantage of the patient's exposure to X-radiation.

BRIEF DESCRIPTION OF THE DRAWINGS

A useful execution and development of the invention can be seen in the subclaims and the following description of one execution example's drawing:

BEST MODE FOR CARRYING OUT INVENTION

Figure 1:
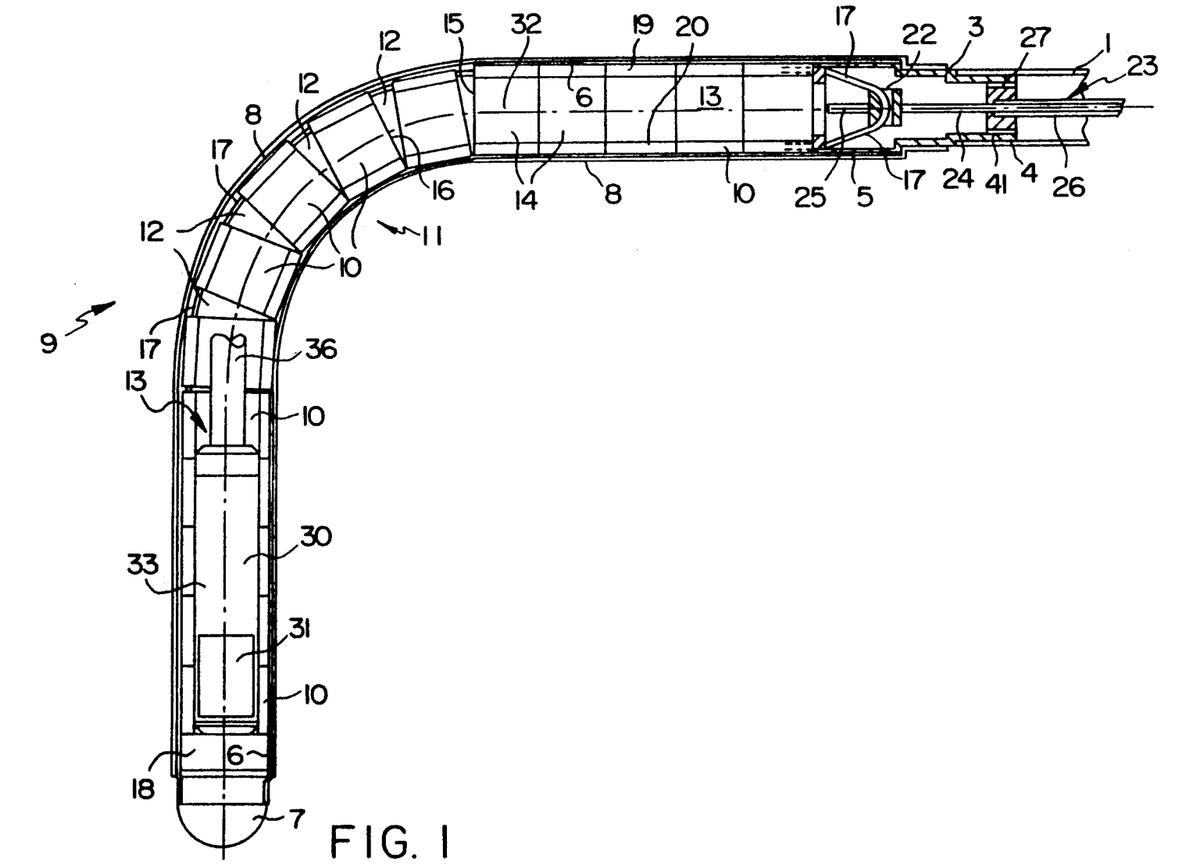
FIG. 1 the distal end of the ultrasound endoscope device according to the invention in its curved position, FIG. 2 a sectional view of the distal end in its rigid and straight position, FIG. 3 an enlarged top view of the carriage for the ultrasound converter, FIG. 4 a side view of the carriage, FIG. 5 a cross section of the ultrasound endoscope device's distal end enlarged approximately five times, FIG. 6 a perspective view of one of the guide links of the distal end of the ultrasound endoscope device open in the direction of the ultrasound's projection, FIG. 7 a cross section similar to FIGS. 1 and 2, with the section between the distal end and the tube of the ultrasound device enlarged and FIG. 8 a manipular device for operating the locking device of the distal end and for moving the ultrasound converter along the distal end's longitudinal axis during scanning.

FIG. 1 shows—in its actual size—the introductory distal end section 9 of an esophagoscope, or esophageal probe, for performing transesophageal echo cardiography. The esophageal probe represents an ultrasound endoscope device and is connected to an ultrasound image processing system not shown in the drawing for obtaining three-dimensional data for a patient's organ in question—especially for a patient's heart.

Figure 8:
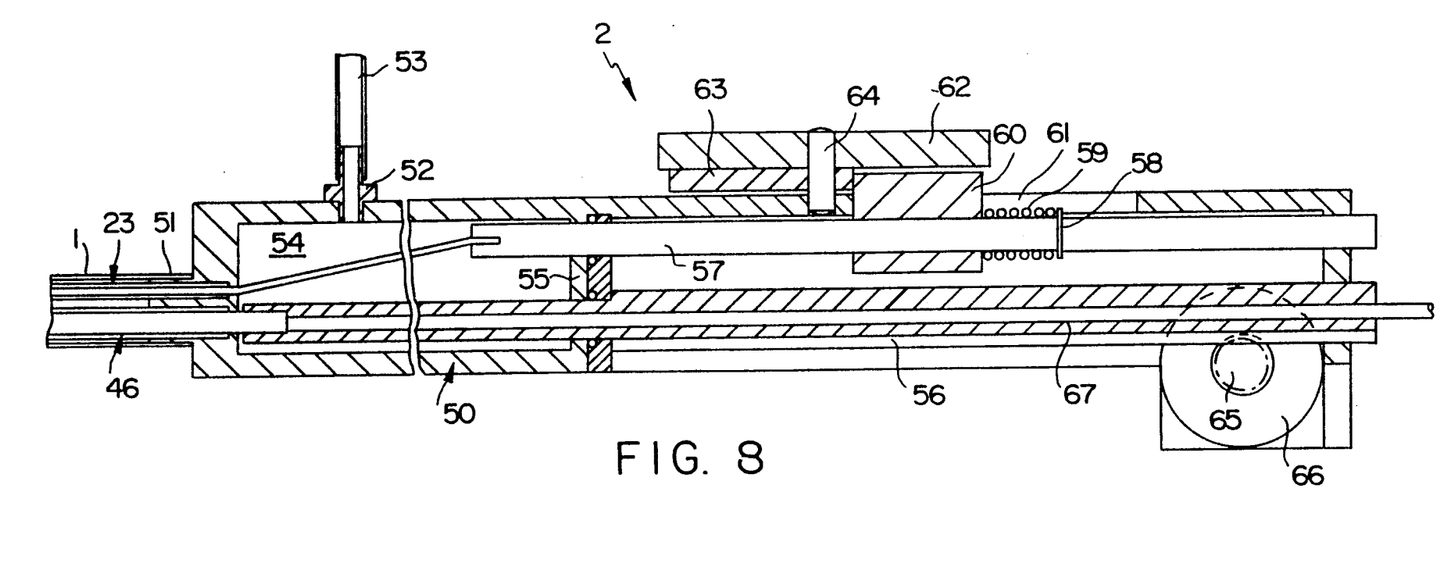

The esophageal probe for transesophageal echo cardiography has a flexible tube 1, of which one end is connected to the esophageal probe as shown in FIG. 1, and the other end connected to the manipulator device 2 shown in FIG. 8.

As can be seen in FIG. 1, the distal end of tube 1 is connected by means of a coupling sleeve 3, which in the example in FIG. 1 consists essentially of three sectional parts of differing widths whereby the cylindrical section 4 is part of tube 1.

The housing section 5 located opposite the cylindrical section 4 is connected to a flexible hose 6—made, for example, of rubber—which extends to a distal end piece 7. If necessary, the flexible hose 6 can have perforations (not shown in drawing) and be surrounded by a tube-like balloon envelope 8, which can be expanded as shown in FIG. 2 by introducing a liquid, especially water.

Figure 2:
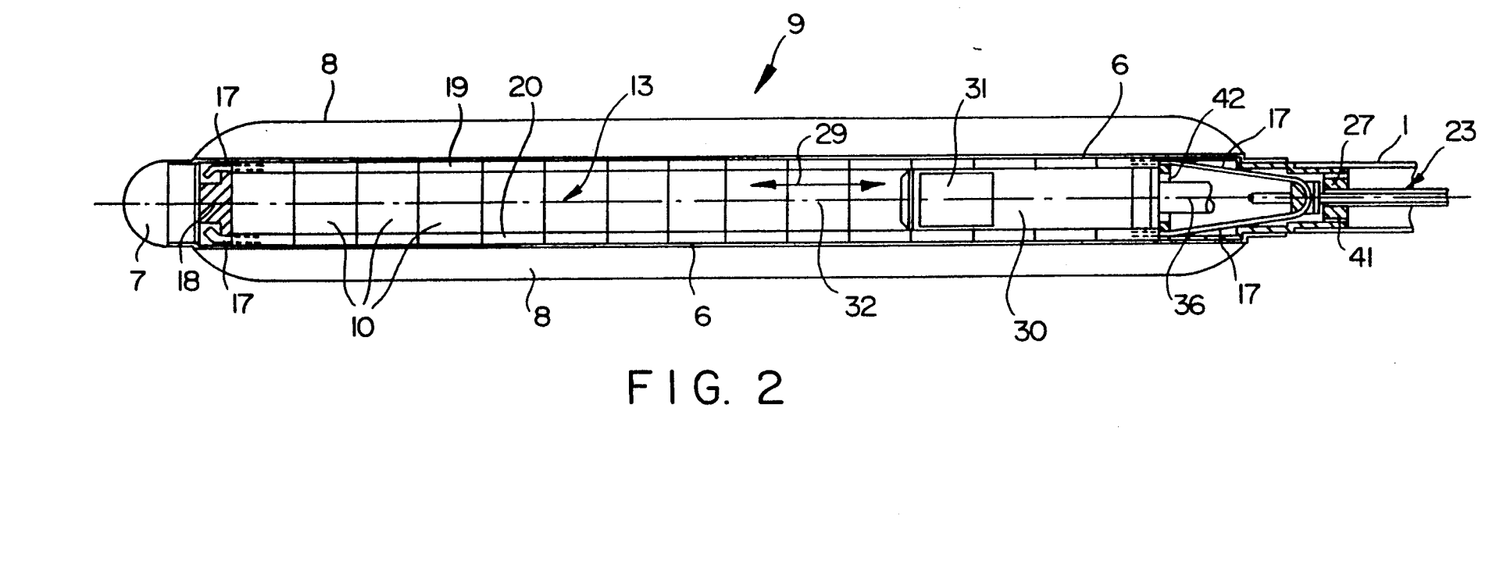

Whereas in FIG. 1 the esophageal probe's distal end section 9 is shown in its curved condition, in FIG. 2 the same section is represented in its straight and rigid position with the balloon envelope 8 expanded. As can be seen from both, FIGS. 1 and 2, the flexible hose 6 encloses a number of approximately 12 mm long rigid guide links 10, the exact shape of which can be recognized more clearly in FIGS. 5 and 6. The flexible hose 6 holds the guide links 10 elastically in their position between the distal end piece 7 and the coupling sleeve 3. The total length of the row of guide links 10 corresponds to the distance between the distal end piece 7 and the housing section 5 and coupling sleeve 3.

As shown in FIG. 1, the esophageal probe's distal end 9 can be bent by applying lateral force on the elastic and flexible hose 6 and a curvature with a radius of about 35 mm attained. When the distal end section is bent, wedge-shaped recesses 12 form in the area of the curvature 11 between the guide links 10 in compensation as shown in FIG. 1. The elastic outer skin of the hose 6 and its sub-division into many relatively short and rigid guide links make the distal end section 9 very flexible and allow easy insertion of the esophageal probe into the patient's esophagus.

Figure 5:
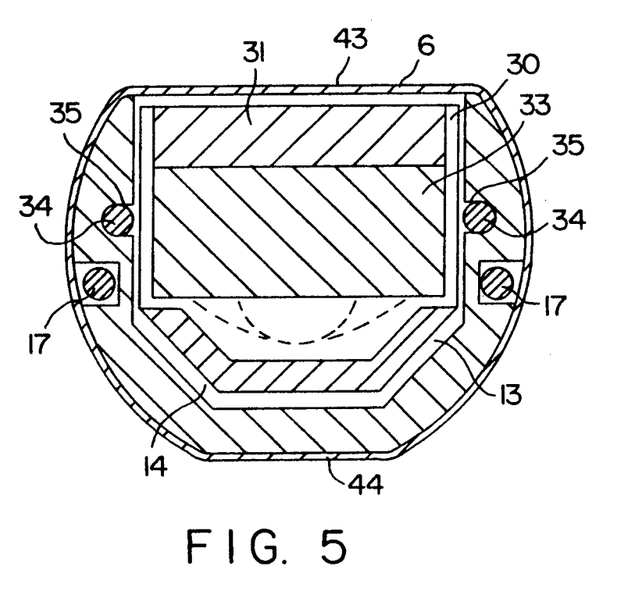
Figure 6:
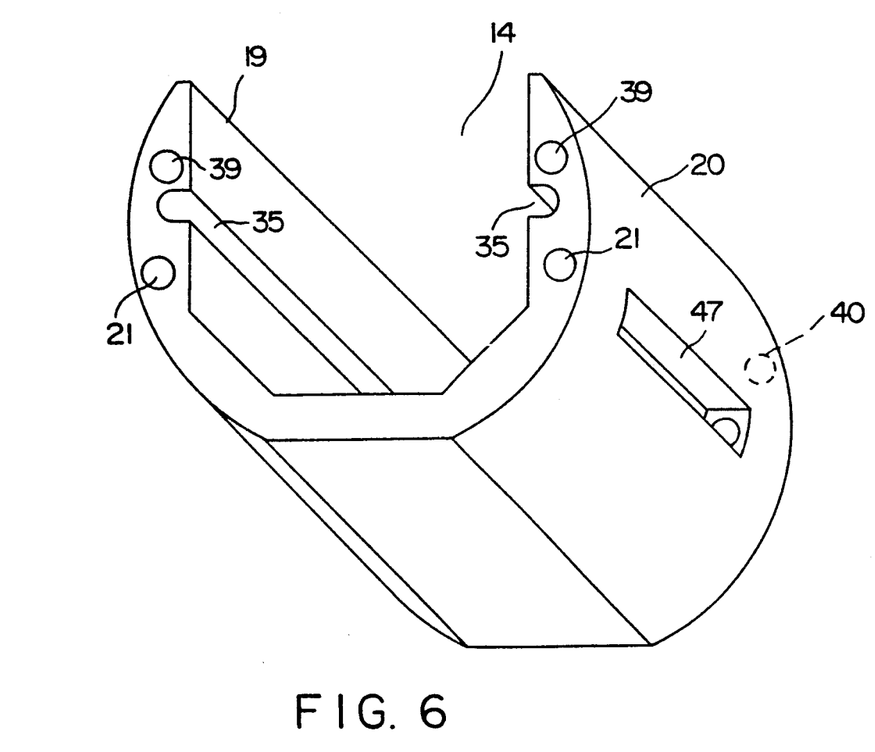

When the guide links 10 are pressed in close contact with each other, as shown in FIG. 2, they form a straight and strong guide channel 13, since all guide links have identical hollow spaces 14, which can be recognized more clearly in FIGS. 5 and 6 than in FIGS. 1 and 2.

In order to change the esophageal probe's distal end section 9 from its curved condition in FIG. 1 to its straight and rigid condition in FIG. 2, the force exerted by the flexible hose 6 is reinforced by means of a locking device by which the guide links 10 are pressed together until their mutual distal frontal faces 15 and their proximate end faces 16 are in close contact with each other. Because the distal frontal faces 15 and the proximate end faces 16 are always at right angles to the longitudinal axis of the guide links 10, the distal end section can be straightened and the flexible hose 6 reverts from a curved to a upright position while the hollow spaces 14 form a precise and straight guide channel 13.

As shown in FIGS. 1 and 2, the essential element of the locking device is a tension wire 17 which—starting from a strain washer 18 at end piece 7—is strung through tension wire holes 21 drilled through the guide links' side walls 19 along their longitudinal axis (see also FIG. 6). The tension wire 17 exits from guide link 10 near the coupling sleeve 3 and continues via a reversing part 22 to tension wire holes 21 in the opposite side walls 20 of guide links 10. Thus, the tension wire 17, held in a mobile manner in reversing part 22, returns to the strain washer 18 where both of its ends are anchored.

The reversing part 22 allows a pulling force to be exerted on the tension wire 17 and thus, simultaneously, on both of its sections that run through the side walls 19 and 20, which is transmitted to the strain washer and presses the guide links 10 toward the coupling sleeve 3. This way, by pulling back on the reversing part 22 and tightening the tension wire 17, the distal end section 9 can be changed from a curved into a straight position and fixed in place by locking the reversing part 22.

Figure 7:
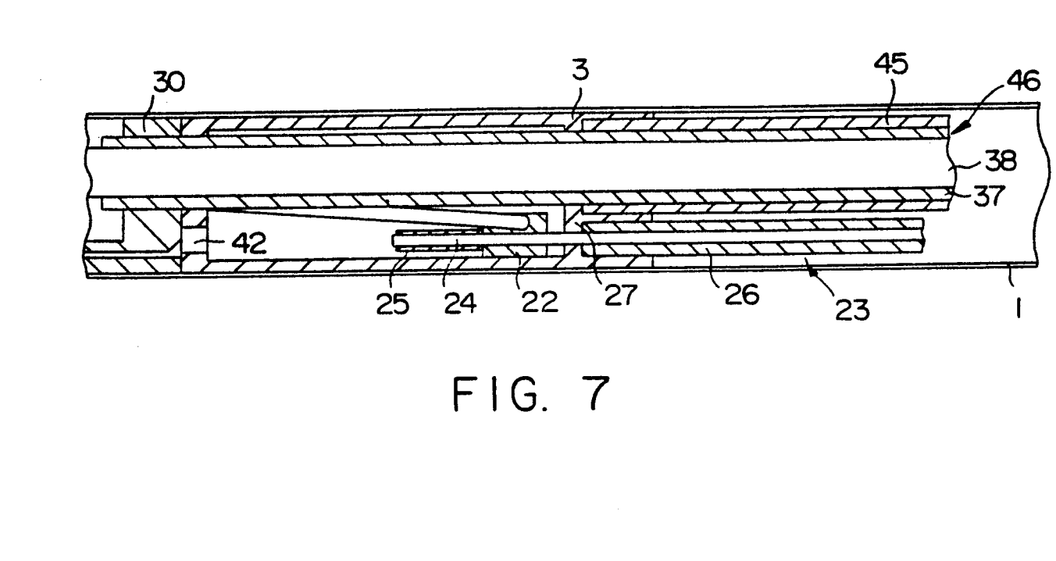

FIGS. 1, 2, and 7 show that in order to exert a pulling force on the tension wire's two sections, a Bowden cable 23 is connected to the reversing part 22 and secured by a bushing 25. The Bowden cable's outer shell 26 is connected to a partition wall 27 in coupling sleeve 3, allowing the exertion of a pulling force via the Bowden cable 23 by means of a manipulator device shown in FIG. 8.

The guide links 10 form a guide channel 13 along which the carriage 30 can move as shown in FIGS. 1 through 4. In FIG. 1, the carriage is shown in its advanced position and in FIG. 2 in its retracted position. When the guide channel is in its straight configuration, as shown in FIG. 2, the carriage 30 can be moved along the channel in direction of the double arrow 29 for a distance of about 130 mm. The carriage 30 carries the ultrasound converter 31—for example, an radiator array—which permits scans of planar sections at right angles to the straight longitudinal axis 32 of the distal end section 9 to obtain radiographic sectional images in the form of tomographs with the help of an ultrasound image processing system connected to the esophageal probe.

Figure 3:
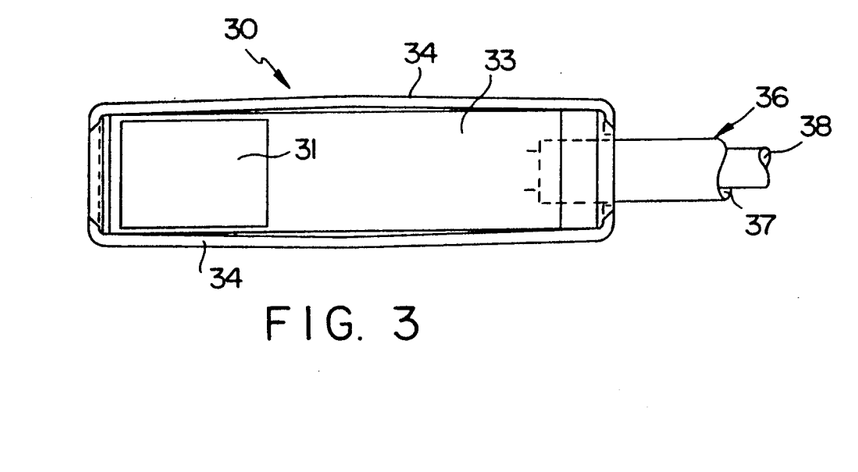
Figure 4:
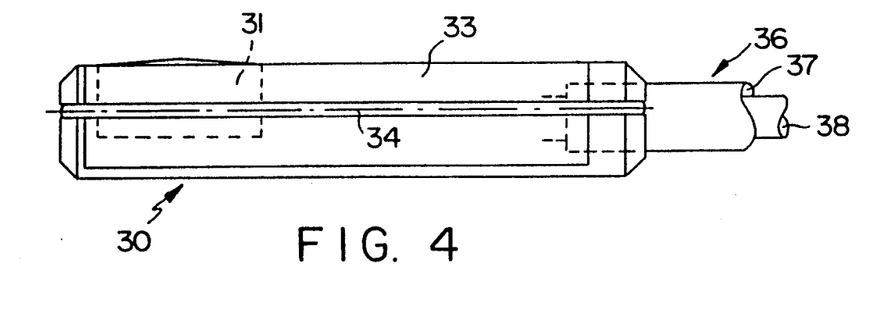

The ultrasound converter is imbedded in a casting compound 33. FIGS. 3 and 4, in which the carriage is represented—compared to FIGS. 1 and 2—twice enlarged, show that the carriage 30 has been provided with a guide bow 34 which guides the carriage 30 with great precision along the guide channel 13 in the direction of the double arrow 29. As shown in FIGS. 5 and 6, the guide links 10 have been provided for that purpose with guide slots 35 to engage the sides of the guide bow 34 which, for example, may consist of elastic wire.

The ultrasound converter 31 is connected via a multi-wire cable 36 which can move lengthwise with the carriage 30 through the distal end section 9 and the tube 1. The cable's other end leads to the manipulator device 2 by which it can be advanced or retracted. In addition, the cable 36 is electrically connected to the ultrasound image processing system in order to be able to take multiple, multiplanar sectional images of the surrounding area of esophageal probe's distal end section 9 from the carriage's many positions.

The cable 36 has a flexible cover 37 which encloses the trunk line 38.

As FIGS. 3 through 6 show, the two ends of of the guide bow 34, the guide slots 35, and the tension wire holes 21 run parallel to the longitudinal axis 32 of the esophageal probe's distal end section 9. In order to make the guide function of the guide bow 35 especially advantageous, the bow can be arched or slightly convex in shape, as shown in FIG. 3, so that it exerts only little lateral force on the side walls 19 and 20 of guide links 10. This way, a particularly reliable guidance can be obtained when the carriage 30 is pulled from the front end of the distal end section 9 toward its proximal end. Alternatively, it is possible to proceed in the reverse direction, that is, to scan in an advancing motion.

Because only one single tension wire 17 is used to stiffen the distal end section 9, both ends of which are fastened to the strain washer 18, it is particularly easy to compensate for any unevenness. It merely requires that lateral movement of the tension wire 17 in the reversing part 22 is kept to a minimum. In order to ensure the guide links' precise alignment when the Bowden cable 23 is activated, their distal faces 15 or their proximal faces 16 have been provided with small elevations 39 which may, for example, have the shape of centering cones to which recesses 40 have been assigned in each of the neighboring proximal faces 16 or distal faces 15, whereby the position of each of the elevations 39 and the recesses 40 has been chosen in such a manner that the elevation 39 of one guide link 10 engages in the recess of the neighboring guide link 10. FIG. 6 shows an additional recess 47 so that the bores of tension wire holes can be short and, therefore, easier to drill.

FIG. 6 represents a single guide link 10 which is open at the top, without the surrounding flexible hose 6 and the inserted carriage 30, while the sectional view in FIG. 5 of the esophageal probe's distal end section 9—also shown without the above mentioned balloon envelope—demonstrates in greater detail the mutual positioning of the various component parts. The remaining hollow space 14 around the carriage in the guide channel 13 is filled with water during the use of the esophageal probe in order to obtain good probe-to-specimen contact. The water is supplied via the tube 1 and the connecting passages 41 in partition wall 27 recognizable in FIGS. 1 and 2. Additional connecting channels 42 for the water supply are provided at the distal end of coupling sleeve 3 which is shown, for example, in FIG. 7.

In the case of one form of the invention's execution—differing from the example shown in FIG. 5—where a balloon envelope 8 is provided for, the top side 43 of hose 6 has perforations by which water can reach the interior of the balloon envelope.

As can be seen especially in FIGS. 5 and 6, the guide links 10 have an essentially U-shaped cross section with the side walls 19 and 20 forming outwardly curved, saucer-shaped, rounded surfaces. On top, the guide links 10 are open and their bottoms are slightly flattened. The guide links' hollow spaces 14 correspond to the shape of the carriage 30 and have, preferably, parallel walls which are fluted towards their bottoms 44. By proceeding in this manner, an especially compact design can be attained as a result, and the outside diameter of the esophageal probe can be kept at a minimum.

As can be seen in FIG. 7, the cable 36, together with the cable conduit 45, form an additional Bowden cable 46 for advancing and retracting the ultrasound converter 31 on its carriage 30.

The conduit 45 of Bowden cable 46, as well as envelope 26 of Bowden cable 23, end in the housing 50 of the manipulator device 2, the cross-section of which is shown in its actual size in FIG. 8. The housing 50 has a connection fitting 51 with holes to admit the Bowden cables 23 and 46 and —although not shown in FIG. 8—for the water supply; and the tube 1 of the esophageal probe can be slipped over the fitting's jacket.

As shown in FIG. 8, the manipulator device 2 has a water inlet fitting 52 to which a water hose can be connected to supply water for improved probe-to-specimen contact. In addition, one can see in this drawing that the water inlet fitting 52 leads into an interior chamber 54 of the manipulator device 2 which has a partition wall 55 through which runs a toothed rack 56 on one side and a connecting rod 57 on the other side. In order to prevent water from leaking through the openings in the partition wall 55, they are sealed with O-rings 58 and 59.

As shown in FIG. 8, the wire 24 of the Bowden cable 23, which serves to align and stiffen the distal end section 9, is attached to the left end of the connecting rod 57. The connecting rod 57 in the housing 50 can be moved lengthwise. FIG. 8 shows, in addition, that the connecting rod has a stop ring attached on which pressure is exerted by a pressure spring 59 and a contact piece 60 assigned to it which can be moved along the connecting rod 57. The contact piece 60 projects to the outside of the housing 50 through a slot 61 from where it can be moved from the left end position in FIG. 8 to the right by means of a handwheel 62 and an eccentric 63 when the handwheel 62 and the eccentric 63 are turned on the axle 64 at the housing 50. In moving the connecting rod to the right, a force is exerted on the tension wire 17 via the Bowden cable 23 which results in straightening and stiffening of the distal end section 9.

The toothed rack 56 can move longitudinally in housing 50 and engages a pinion gear 65 which is driven by a pulse motor 66. Depending on the direction of rotation of the pulse motor 66, the toothed rack 56 is moved and the Bowden cable 46, which is attached in FIG. 8 to the left end of the toothed rack 56, is activated. The flexible cover 37 of cable 36 is firmly attached to the toothed rack 56. The electric trunk line 38 of cable 36 runs through a cable channel 67 in the toothed rack 56 and exits the manipulator device 2 in FIG. 8 at the right side of housing 50 and toothed rack 56. The pulse motor 66 is controlled by a computer at the image processing system, and stop-and-go, incremental steps, and delay functions are adjustable based on EKG trigger impulses. The incrementational steps for the individual planar sections are adjusted at 0.5 mm.

We claim:

1. An ultrasound endoscope device for scanning the patient's organ in question, in particular, for use in transesophageal echo cardiography, comprising:

an ultrasound converter which is electrically connected via an ultrasound diagnostic device to an image processing system for producing multiplanar tomograms, and which is arranged in a mobile manner in the distal end section of the endoscope device,;

a flexible hose having a balloon envelope serving as a water supply line surrounding said distal end section;

a plurality of axially aligned rigid guide links formed to have hollow spaces open to one side to facilitate sound projection, said hollow spaces being defined by end faces and side walls adapted to form a continuous guide channel;

a mobile carriage for carrying the ultrasound converter, directed within said guide channel by a plurality of guide elements through said hollow spaces;

a tension wire running through the guide links by which the guide links can be pressed together at opposing ones of said faces; and manipulator means attached to the proximal end of the endoscope device, including a first Bowden cable assigned to the tension wire and a second Bowden cable assigned to the carriage, the manipulator means further including a tube member and a water supply fitting through which water can be supplied to said distal end section.

2. An ultrasound endoscope device according to claim 1, wherein:

the guide links are arranged between a strain washer and a coupling sleeve along two sections of tension wire which run through bore holes in two opposite walls of each of the guide links and which sections of tension wire are connected at their middle section to said first Bowden cable.

3. An ultrasound endoscope device according to claim 1, wherein:

the guide links have at their opposite faces a plurality of elevations and recesses which engage with the respective plurality of elevations and recesses of the neighboring guide link when said distal end section is in straight and rigid condition.

4. An ultrasound endoscope device according to claim 1, wherein:

said side walls of the guide links have guide slots provided within said hollow spaces along which the carriage for the ultrasound converter is moved.

5. An ultrasound endoscope device according to claim 4, wherein:

the carriage includes guide bow means projecting laterally therefrom for engaging said guide slots.

6. An ultrasound endoscope device according to claim 5, wherein:

said guide bow means has a slightly convex shape and is elastic.

7. An ultrasound endoscope device according to claim 1, wherein:

the flexible hose includes perforations formed therethrough to facilitate fluid delivery to the interior of said balloon envelope.

8. An ultrasound endoscope device according to claim 1, wherein:

said first Bowden cable assigned to said tension wire is connected to a lengthwise movable connecting-rod which can be moved or locked in place by means of an eccentric.

9. An ultrasound endoscope device according to claim 1, wherein:

said second Bowden cable assigned to the carriage is connected to a toothed rack which is driven by a pulse motor and by which the carriage and the ultrasound converter can be advanced at the start of a scanning series and retracted or advanced toward the proximal end of the endoscope device at a predetermined increment after each scanning.

* * * * *